United States Patent [19]

Shankar et al.

[11] Patent Number: 4,937,350
[45] Date of Patent: Jun. 26, 1990

[54] PREPARATION OF N-(-3(((ARYL)AMINO)SULDONYL)-1H-1,2,4-TRIAZOL-5-YL)AMINES

[75] Inventors: Ravi B. Shankar; R. Garth Pews, both of Midland, Mich.

[73] Assignee: The Dow Chemical Company, Midland, Mich.

[21] Appl. No.: 361,618

[22] Filed: Jun. 5, 1989

[51] Int. Cl.$^5$ ............................................. C07D 249/12
[52] U.S. Cl. .................................. 548/263.8; 548/263
[58] Field of Search ................................ 548/263, 265

[56] References Cited
U.S. PATENT DOCUMENTS

| 4,734,123 | 3/1988 | Monte ........................................ 71/92 |
| 4,740,233 | 4/1988 | Kleschick et al. ........................ 71/92 |
| 4,818,273 | 4/1989 | Kleschick et al. .................... 548/263 |

OTHER PUBLICATIONS

Rowson et al, "Preparation of Aryltriozole, etc", CA 108:94569r (1988).
Jelich et al, "Preparation of [1,2,4]triazolo, etc", CA 109:93057f (1988).

Primary Examiner—Glennon H. Hollrah
Assistant Examiner—Patricia L. Morris
Attorney, Agent, or Firm—Craig E. Mixan; Ronald G. Brookens

[57] ABSTRACT

N-(3-(((2,6-Dihalophenyl)amino)sulfonyl)-1H-1,2,4-triazol-5-yl)amines, intermediates for the preparation of herbicidal substituted 1,2,4-triazolo(1,5-a)pyrimidine-2-sulfonanilides, are directly prepared from an appropriately substituted 4-bromoaniline and a protected 5-amino-1,2,4-triazole-3-sulfonyl chloride. The improved reaction scheme involves the individual reaction steps of (a) coupling, (b) halogenation and (c) reduction.

7 Claims, No Drawings

PREPARATION OF N-(-3(((ARYL)AMINO)SULDONYL)-1H-1,2,4-TRIAZOL-5-YL)AMINES

FIELD OF THE INVENTION

The present invention is directed to a process for the preparation of N-(3-(((2,6-dihalophenyl)amino)sulfonyl)-1H-1,2,4-triazol-5-yl)amines. More particularly, the present invention is directed to a process for the preparation of such amines from 4-bromoanilines.

BACKGROUND OF THE INVENTION

Substituted 1,2,4-triazolo(1,5-a)pyrimidine-2-sulfonanilides (I)

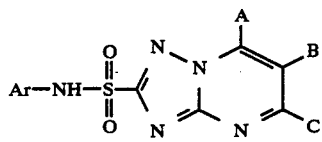

such as those described in U.S. Pat. No. 4,740,233, are valuable herbicides for the selective control of weeds in agronomic crops. Compounds of this family have generally been prepared by the conventional reaction between an appropriately substituted aniline (II) and a substituted 1,2,4-triazolo(1,5-a)pyrimidine-2-sulfonyl chloride (III)

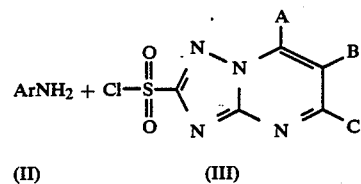

in the presence of a tertiary amine base (U.S. Pat. No. 4,740,233) or an excess of the aniline (British Patent No. 951,652). This procedure is generally satisfactory for the preparation of substituted 1,2,4-triazolo-(1,5-a)pyrimidine-2-sulfonanilides when the substituted aniline employed is aniline itself or is a substituted derivative of aniline that has similar reactivity as a nucleophilic reagent. When the substituted aniline reactant is of substantially reduced nucleophilic reactivity due to the presence of electron-withdrawing substituents on the ring, and especially, to the presence of such substituents in the positions ortho to the amino function, this method is very slow and provides low yields of the desired products. This reactivity problem is particularly unfortunate because the most herbicidally potent substituted 1,2,4-triazolo-1,5-a)pyrimidine-2-sulfonanilides possess such substituents.

In order to circumvent the reactivity problem, a strong base, such as an alkali metal alkyl or an alkali metal hydride, capable of converting the poorly nucleophilic substituted aniline to its corresponding metal derivative, is employed in place of the tertiary amine base as described in U.S. Pat. No. 4,740,233. The metal derivative is preformed and then allowed to react with a substituted 1,2,4-triazolo(1,5-a)pyrimidine-2-sulfonyl halide. This procedure allows the compounds to be prepared, but it requires an excess of the metal derivative of the substituted aniline and is carried out below 0° C., and, therefore, is not commercially desirable.

For 1,2,4-triazolo(1,5-a)pyrimidine-2-sulfonanilides bearing heterocyclic substituents (A, B and C) which are incompatible with reaction conditions for the preparation of the 1,2,4-triazolo(1,5-a)pyrimidine-2-sulfonyl halide or the subsequent sulfonamide, an alternative procedure involving the intermediacy of N-(3-(((aryl)amino)sulfonyl)-1H-1,2,4-triazol-5-yl)amines (IV) (IV)

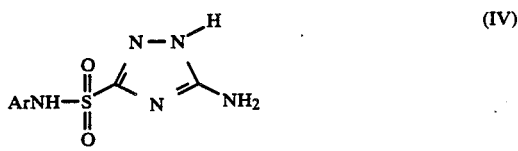

is recommended in U.S. Pat. Nos. 4,740,233 and 4,734,123. In this case, 1,2,4-triazolo(1,5-a)-pyrimidine-2-sulfonanilides bearing heterocyclic substituents compatible with the reaction chemistry are first prepared. These materials are then subjected to oxidative ring cleavage and hydrolysis to afford N-(3-(((aryl)amino)-sulfonyl)-1H-1,2,4-triazol-5-yl)amines (IV) which can undergo cyclization with substituted 1,3-dicarbonyl compounds to form the desired 1,2,4-triazolo(1,5-a)pyrimidine-2-sulfonanilide.

In view of the valuable herbicidal properties of the sulfonanilides (I), it is highly desirable to have a direct process for the preparation of N-(3-(((aryl)amino)sulfonyl)-1H-1,2,4-triazol-5-yl)amine intermediates (IV) which can be used to prepare a wide range of materials having a variety of heterocyclic substituents. It is also desirable that this process be capable of producing N-(3-(((aryl)amino)sulfonyl)-1H-1,2,4-triazol-5-yl)amines in which the aryl groups contain electron-withdrawing substituents without resorting to exceedingly long reaction times or the need of a strong base, such as an alkali metal alkyl or an alkali metal hydride.

SUMMARY OF THE INVENTION

The present invention relates to a novel method of preparing N-(3-(((2,6-dihalophenyl)amino)sulfonyl)-1H-1,2,4-triazol-5-yl)amines of Formula V

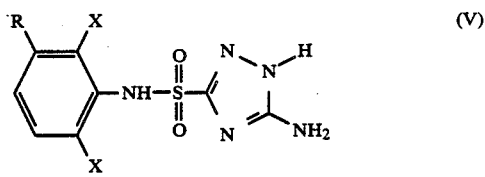

wherein
R represents H, $C_1$–$C_4$ alkyl or $C_1$–$C_4$ alkoxy: and X independently represents Cl or Br.

It has been found that the intermediates (V) can be directly prepared in good yield from a 4-bromoaniline (VI) and a 5-amino-1,2,4-triazole-3-sulfonyl chloride derivative (VII) by the following reaction scheme.

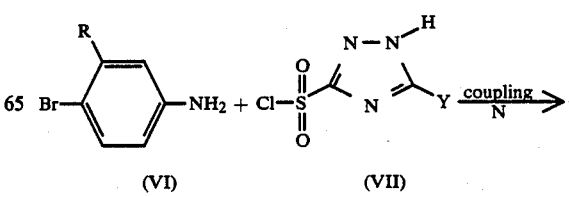

-continued

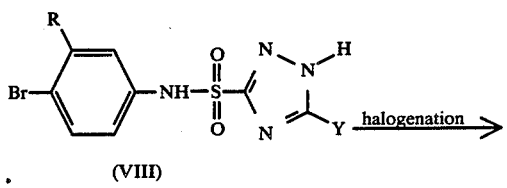

(VIII)

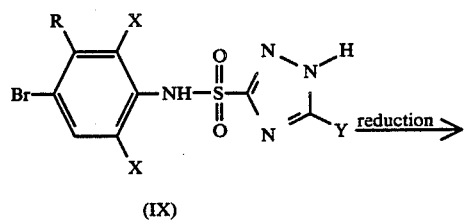

(IX)

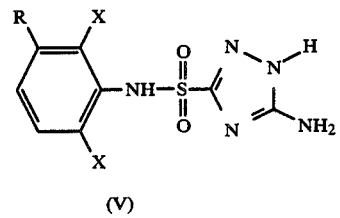

(V)

In this scheme,
R and X are as previously defined, and
Y represents —NH$_3$⊕X⊖ or

and
R$^1$ represents H, C$_1$–C$_4$ alkyl or phenyl.

According to the present invention, the improved process is comprised of the following steps:

(a) coupling a 4-bromoaniline of the formula (IV)

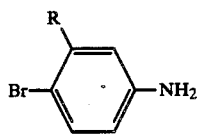
(VI)

wherein
R represents H, C$_1$–C$_4$ alkyl or C$_1$–C$_4$ alkoxy with a protected 5-amino-1,2,4-triazole-3-sulfonyl chloride of the formula (VII)

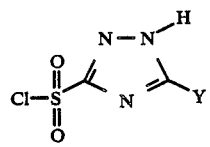
(VII)

wherein
Y represents —NH$_3$⊕X⊖ or

and
R$^1$ represents H, C$_1$–C$_4$ alkyl or phenyl to produce a protected N-(3-(((4-bromophenyl)amino)sulfonyl)-1H-1,2,4-triazol-5-yl)amine of the Formula (VIII)

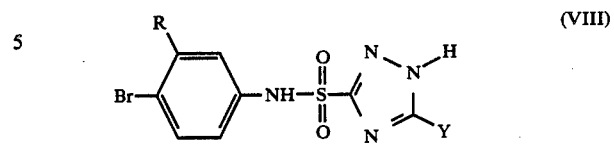
(VIII)

wherein
Y, R and R$^1$ are as previously defined;

(b) halogenating the protected N-(3-(((4-bromophenyl)amino)sulfonyl)-1H-1,2,4-triazol-5-yl)amine (VIII) with chlorine or bromine to produce a protected N-(3-(((4-bromo-2,6-dihalophenyl)amino)sulfonyl)-1H-1,2,4-triazol-5-yl)amine of the Formula (IX)

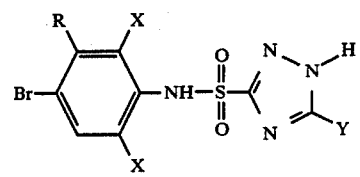
(IX)

wherein
Y, R and R$^1$ are as previously defined, and
X independently represents Cl or Br; and (c) reducing the protected N-(3-(((4-bromo-2,6-dihalophenyl)amino)sulfonyl)-1H-1,2,4-triazol-5-yl)amine (IX) to produce the N-(3-(((2,6-dihalophenyl)amino)sulfonyl)-1H-1,2,4-triazol-5-yl)amine of the Formula (V)

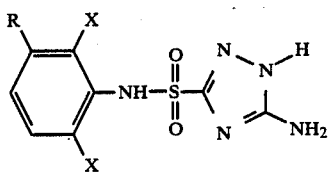
(V)

wherein
X, Y, R and R$^1$ are as previously defined.

By halogenating subsequent to the coupling reaction, it has been found the aniline (VI), absent electron-withdrawing groups in the 2- and 6-positions, is readily coupled with the sulfonyl chloride (VII) in the presence of only a tertiary amine base or of an excess of the aniline itself. After specific halogenation in the 2- and 6-positions of the phenyl ring, it has been found that the 4-bromo group can be selectively reduced to provide the desired N-(3-(((2,6-dihalophenyl)amino)sulfonyl)-1H-1,2,4-triazol-5-yl)amines (V). The present invention provides the desired intermediates directly, in good yield and without the need of a strong base.

DETAILED DESCRIPTION OF THE INVENTION

As used herein, the term "halogen" refers to chlorine and bromine. The preferred halogen is chlorine.

The terms "C$_1$–C$_4$ alkyl" or "C$_1$–C$_4$ alkoxy" refer to straight-chained or branched hydrocarbon groups of up to four carbon atoms, provided that all substituent groups are sterically compatible with each other. The term "sterically compatible" is employed to designate substituent groups which are not affected by steric hindrance as this term is defined in "The Condensed Chemical Dictionary", 7th edition, Reinhold Publishing Co., N.Y. page 893 (1966) which definition is as follows: "steric hindrance. A characteristic of molecular structure in which the molecules have a spatial arrangement of their atoms such that a given reaction with another molecule is prevented or retarded in rate."

Sterically compatible may be further defined as reacting compounds having substituents whose physical bulk does not require confinement within volumes insufficient for the exercise of their normal behavior as discussed in Organic Chemistry of D. J. Cram and G. Hammond, 2nd edition, McGraw-Hill Book Company, N.Y., page 215 (1964).

The preferred "$C_1$-$C_4$ alkyl" and "$C_1$-$C_4$ alkoxy" groups are —$CH_3$, —$CH_2CH_3$, —$OCH_3$ and —$OCH_2CH_3$. The most preferred group is —$CH_3$.

Y is preferably —NHC(O)$R^1$ and $R^1$ is preferably H, —$CH_3$ or phenyl.

The 4-bromoaniline starting materials (VI) are known compounds or can be prepared by the bromination of the appropriate 3-alkyl- or 3-alkoxyanilines, or by the bromination of the corresponding acetanilide followed by hydrolysis back to the aniline.

The protected 5-amino-1,2,4-triazole-3-sulfonyl chlorides (VII) in which Y represents -NHC(O)$R^1$ and in which $R^1$ represents H, $C_1$-$C_4$ alkyl or phenyl can be prepared by reacting 5-amino-3-mercapto-1,2,4-triazole with the appropriate carboxylic acid ($R^1$COOH) or the corresponding anhydride, ester or acid halide under conventional amide-forming conditions. Functionally, the Y group represents a protected amino group which is necessary to prevent intramolecular self-condensation once the mercapto group is converted into a sulfonyl chloride. The mercaptan can be converted to the sulfonyl chloride by oxidation with chlorine in aqueous hydrochloric acid or other aqueous organic media.

In the coupling reaction, a 4-bromoaniline (VI) is reacted with a protected 5-amino-1,2,4-triazole-3-sulfonyl chloride (VII) in the presence of a base. The base may be a tertiary amine base or an excess of the aniline itself. At least one equivalent of base is required for each equivalent of the sulfonyl chloride. The base serves as an acceptor of the byproduct HCl. If the 4-bromoaniline is itself employed as the base, at least two equivalents of the aniline are required, one to react with the sulfonyl chloride and one to react with the HCl liberated. It is preferred to employ excess bromoaniline as the base. Molar ratios of 2:1 to 3:1 of bromoaniline to sulfonyl chloride are most preferred.

The coupling reaction is preferably carried out in the presence of polar aprotic organic solvents which are inert to the reaction conditions. Preferred solvents include but are not limited to alkylnitriles, such as, for example, acetonitrile: ethers, such as, for example, tetrahydrofuran; and carboxylic acid esters, such as, for example, ethyl acetate.

The coupling reaction is generally run from about 40° to about 150° C., preferably from about 60° to about 125° C. The temperature is conveniently maintained at a particular range by operation at the reflux temperature of the solvent.

The coupling reaction is preferably conducted under an inert atmosphere, such as, for example, under a nitrogen or argon blanket. Although conveniently conducted at atmospheric pressure, the reaction is preferably run under a slight positive pressure of up to about 5 pounds per square inch (psi) of the blanketing inert gas which helps in keeping the reaction mixture dry.

In a typical reaction, two equivalents of the 4-bromoaniline and one equivalent of the protected 5-amino-1,2,4-triazole-3-sulfonyl chloride are dissolved in a polar aprotic organic solvent and refluxed under a nitrogen atmosphere until the reaction is complete, generally in from about one to about eight hours (hr). The reaction mixture is cooled and the precipitated product can be recovered by conventional techniques. The product can be isolated, for example, by filtration, washing with an aqueous acid and drying.

In the halogenation reaction, the protected N-(3-(((4-bromophenyl)amino)sulfonyl)-1H-1,2,4-triazol-5-yl)amine (VIII) is reacted with chlorine or bromine to selectively halogenate in the activated 2- and 6-positions of the sulfonanilide ring. At least one equivalent of halogen is required for each ring position halogenated. The 2- and the 6-positions are not necessarily equivalent, and, depending upon the size of the substituent in the 3-position, it is possible to place a larger bromine substituent in the less crowded 6-position and a smaller chlorine substituent in the more hindered 2-position. If the same halogen is desired in both the 2- and 6-positions, an excess of the halogen can be preferentially employed. Typically, molar ratios ranging from about a 2.2 to about a 6 fold excess of halogen are employed.

Because the sulfonanilide ring is activated towards electrophilic aromatic substitution, the halogenation reaction is relatively facile and is conducted at a temperature from about ° 5 to about 65° C. Temperatures from about 10° to about 30° C. are preferred.

The protected N-(3-(((4-bromophenyl)amino)sulfonyl)-1H-1,2,4-triazol-5-yl)amines (VIII) are only sparingly soluble in most solvents. Therefore, the halogenation reaction is generally conducted in relatively dilute solutions containing from about 1 to about 5 percent of substrate (VIII). Suitable solvents are polar organic solvents that are miscible with water and are not readily halogenated themselves. Such solvents include, for example, lower alkylnitriles like acetonitrile. Mixtures of these polar organic solvents with water are the preferred reaction medium.

In a typical halogenation reaction, the protected N-(3-(((4-bromophenyl)amino)sulfonyl)-1H-1,2,4-triazol-5-yl)amine is dissolved in a mixture of a polar organic solvent and water. The solution, cooled in an ice bath, is rapidly stirred as the halogen is introduced. The reaction mixture is stirred from about 1 to about 3 hr at ambient temperature, and the product is isolated by conventional procedures. For example, in most cases the product precipitates from the reaction mixture and may simply be isolated by filtration and drying.

In the reduction step, a protected N-(3-(((4-bromo-2,6-dihalophenyl)amino)sulfonyl)-1H-1,2,4-triazol-5-yl)amine (IX) is reacted with hydrogen in the presence of a supported noble metal catalyst. During the course of the reaction, the bromine in the 4-position is selectively replaced by hydrogen and the protecting group is removed providing the free amine. By a supported noble metal catalyst is meant any noble metal catalyst on a variety of supports that effects the reduction of the bromo substituent and deprotection of the amine. Such catalysts include but are not limited to platinum, palladium and ruthenium. Typical supports include silica, alumina, magnesia and carbon. The preferred catalysts are platinum and palladium supported, for example, on carbon. The most preferred catalysts range from about 0.5 to about 10 percent palladium on carbon. Generally, about 0.001 to about 0.05 equivalents of noble metal are employed per equivalent of (IX); from about 0.01 to about 0.03 equivalents are preferred.

The reduction is conveniently conducted with an excess of hydrogen. For example, hydrogen gas can be continuously sparged into the reaction mixture at atmospheric pressure. Alternatively, a sealed reactor can be pressurized with hydrogen gas.

The reduction is generally performed in an organic solvent that is inert to the reaction conditions. Alcohols, such as, for example, ethanol, propanol and butanol, are particularly preferred.

The reduction is carried out at a temperature from about 0° to about 150° C., preferably from about 75° to about 125° C. The temperature is conveniently maintained at a particular range by operation at the reflux temperature of the solvent. Operating pressures are not critical and may vary from atmospheric pressure to superatmospheric. Atmospheric pressure is satisfactory and is preferred.

In a typical reduction reaction, a protected N-(3-(((4-bromo-2,6-dihalophenyl)amino)sulfonyl)-1H-1,2,4-triazol-5-yl)amine (IX) is dissolved in an alcohol. The solution is rapidly stirred and purged with nitrogen, and the supported noble metal catalyst is added. The mixture is heated to reflux while hydrogen is continuously introduced. After completion of the reaction, the mixture is purged with nitrogen and filtered to remove the supported catalyst. The product can be conveniently isolated by evaporation of the filtrate.

The following examples are presented to illustrate the invention and should not be construed as limiting the scope of the invention. All melting points are uncorrected.

EXAMPLE 1

Preparation of 5-Amino-3-chlorosulfonyl-1,2,4-triazole [Formula VII: Y=-NH$_2$]

5-Amino-3-mercapto-1,2,4-triazole [58 grams (g), 0.50 mole] and 400 milliliter (mL) of 10 percent aqueous hydrochloric acid were placed in a reaction vessel equipped with a fritted gas inlet tube, stirrer, thermometer, and gas outlet which was immersed in a dry ice/isopropyl alcohol bath. When the temperature of the mixture dropped to $-10°$ C., chlorine was added through the gas addition tube with stirring and cooling. In all 113 g (1.6 moles) was added over a 50 minute (min) period at $-7°$ to $-11°$ C. The initial slurry became thin and then thick again and the color changed first to a yellow-orange and then back to pale yellow. The resulting slurry was allowed to warm to 15° C. over a 1 hr period and was then filtered to collect the solids. This solid appeared to dissolve in water with some gas evolution and then reprecipitate as an orange solid. It was recovered by filtration and air dried to obtain 16.8 g (18 percent of theory) of the title compound melting at 157.5°–158° C. (dec.).

Elemental analysis: Calc. for C$_2$H$_3$ClN$_4$O$_2$S: %C, 13.2: %H, 1.66; %N, 30.7; Found %C, 13.2; %H, 1.79; %N, 30.5

The carbon-13 nmr spectrum had absorptions at 161.5 and 158.8 ppm, tentatively assigned to the carbon atoms at the 3- and 5-positions, respectively. The compound in hot aqueous hydrochloric acid decomposed to 5-amino-3-chloro-1,2,4-triazole and sulfur dioxide and hydrolyzed to 5-amino-1,2,4-triazole-3-sulfonic acid, a compound decomposing on heating at above 330° C. These compounds had nmr spectra consistent with the assigned structures.

EXAMPLE 2

Preparation of 5-Amino-3-chlorosulfonyl-1,2,4-triazole

A 1 liter (L) bottom draining glass reactor was equipped with a fritted glass gas inlet tube, a gas outlet with a sulfuric acid scrubber, a paddle stirrer, a thermometer, and a jacket connected to a recirculating, temperature-regulated bath maintained at 18° C. A mixture containing 116 g (1.0 mole) of 5-amino-3-mercapto-1,2,4-triazole and 800 mL of 20 percent aqueous hydrochloric acid (made from 432 mL of 37 percent hydrochloric acid and 368 mL of water) was placed in the reactor and 222 g (3.13 moles) of chlorine was added through the gas inlet tube with stirring and cooling over a 165 min period. The temperature of the mixture was maintained at about 22° to about 32° C. under these conditions. The color of the mixture was changeable in the pale yellow to orange range and the initial slurry first thinned out and then became thick again as the reaction proceeded. After all the chlorine was added (uptake and the exotherm ceased), the temperature was reduced to about 5° C. and the mixture was removed through the bottom drain. The solids were collected by filtration, washed with 500 mL of cold water, and air dried to obtain 124 g (68 percent of theory) of the title compound as a pale yellow solid melting at 169.5°–170° C. (dec.). This material was analyzed to consist of 95.5 percent of the title compound and of about 4.5 percent of the corresponding sulfonic acid.

EXAMPLE 3

Preparation of 5-Benzamido-3-mercapto-1,2,4-triazole

To a suitably equipped reaction vessel was charged 116 g (1.0 mole) of 5-amino-3-mercapto-1,2,4-triazole and 500 mL of pyridine. A total of 147.5 g (1.05 mole) of benzoyl chloride was added with vigorous stirring over 25 min, during which time the temperature rose from 24° to 59° C. The mobile, pale yellow slurry obtained was heated at reflux with stirring. The solid material dissolved and then, after about 40 additional min, a white solid began separating. An additional 200 mL of pyridine was added to aid mixing and the reaction was continued at 117°–122° C. for a total of 7 hr. The thick, white slurry obtained was filtered, washed with water and with methylene chloride, and dried to obtain 186 g (84 percent of theory) of the title compound, m.p. 311°–312° C. (dec.).

Elemental analysis (typical sample): Calc. for C$_9$H$_8$N$_4$OS %C, 47.4: %H, 3.92: %N, 24.6; Found: %C, 47.5; %H, 3.61; %N, 24.4;

$^{13}$C NMR:$\delta$=165.90, 165.40, 145.00, 132.68, 131.98; 128.56, and 127.96.

$^1$H NMR: $\delta$=8.50–7.90 (m, 2H) and 7.72–7.61 (m, 3H).

EXAMPLE 4

Preparation of Benzamido-3-chlorosulfonyl-1,2,4-triazole [Formula VII: Y=-NHC(O)Phenyl]

A reactor was charged with 61 g (0.28 mole) of 5-benzoylamino-3-mercapto-1,2,4-triazole and 1 L of 1N hydrochloric acid. The resultant slurry was chilled to $-5°$ C., and a total of 83 g (0.8 mole) of chlorine gas was added through a fritted glass sparger over 40 min while maintaining the temperature at −6° to 4° C. by means of an ice/salt bath. The resulting solids were recovered by filtration, washed with cold water, and dried to obtain 64 g (80 percent of theory) of the title compound as a pale yellow solid, m.p. 203°–205° C. (dec.). A sample purified by recrystallization from acetonitrile gave white needles melting at 209°–210° C. The carbon nmr spectrum was consistent with the assigned structure.

EXAMPLE 5

Preparation of 5-Benzoylamino-3-chlorosulfonyl-1,2,4-triazole

In a manner similar to that described in Example 4, 66 g (0.3 mole) of 5-benzoylamino-3-mercapto-1,2,4-triazole in 1.5 L of 40 percent aqueous acetic acid was chlorinated over 30 min at −2° to +1° C. with 64 g (0.9 mole) of gaseous chlorine to obtain a slurry, which after filtering, washing with water, and drying in a vacuum oven at 50°–55° C. for 24 hr produced a total of 74 g (86 percent of theory) of the title compound melting at 200°–203° C. (dec.).

EXAMPLE 6

Preparation of 5-Acetamido-3-mercapto-1,2,4-triazole

To a 2 L, 3-necked flask equipped with an efficient stirrer, reflux condenser, and thermometer was added 116 g (1.0 mole) of 5-amino-3-mercapto-1,2,4-triazole, 1 L of glacial acetic acid and 153 g (1.5 moles) of acetic anhydride. The mixture was heated to reflux (118°–120° C.) with stirring for 2 hr and then cooled to about 10° C. Recovery of the solids present by filtration and drying resulted in about 102 g (65 percent of theory) of the title compound, m.p. 326°–328° C. (dec.), a white, crystalline solid. A sample purified by washing with 2-propanol and drying melted at 336° C. (dec.). The carbon nmr spectrum of this compound was consistent with the assigned structure, having absorptions at 169.29, 164.99, 144.77, and 22.73 ppm as were the proton nmr spectrum, having an absorption at −2.00 ppm, and the elemental (C, H, and N) analysis.

EXAMPLE 7

Preparation of 5-Acetamido-3-chlorosulfonyl-1,2,4-triazole [Formula VII: Y=-NHC(O)CH$_3$]

A 3 L, 3-necked flask equipped with an efficient stirrer, thermometer, cooling bath, fritted glass gas inlet tube and aqueous sodium hydroxide scrubber was charged with 79 g (0.5 mole) of 5-acetylamino-3-mercapto-1,2,4-triazole and 250 mL of 10 percent aqueous hydrochloric acid. The mixture was chilled to −5° C. and chlorine gas addition was initiated with good stirring. A total of 114 g (1.6 mole) of chlorine was added over 1.7 hr with the temperature being maintained at −3° to −10° C. The mixture was allowed to stir briefly while warming to 15° C. and was then filtered. The solids obtained were washed with cold water and dried to obtain the title compound as a white solid melting at 184°–184.5° C. The yield was 90.4 g (81 percent of theory). The carbon nmr spectrum was consistent with the assigned structure, having absorptions at 161.0, 151.3, 170.8, and 22.9 ppm.

A sample of this compound was purified by dissolving it in acetone, filtering to remove solids, and removing the acetone by evaporation. It melted at 177° C. with decomposition.

Calc. for C$_4$H$_4$ClN$_4$O$_3$S % C, 21.5; %H, 1.80; %N, 25.1; Found %C, 21.3: %H, 2.20; %N, 25.1.

EXAMPLE 8

Preparation of 5-Formamido-3-mercapto-1,2,4-triazole

A 500 mL, 3-necked flask equipped with a mechanical stirrer, a reflux condenser with nitrogen outlet and a thermometer was charged with 24.4 g (0.2 mole) of 95 percent pure 5-amino-3-mercapto-1,2,4-triazole and 140 mL of formic acid. The mixture was heated to reflux with stirring for 4 hr and allowed to cool to room temperature. The solids present were collected by filtration, washed with water, and dried to obtain 28.2 g (98 percent of theory) of the title compound as a white solid, m.p. 260°–262° C. The infrared spectrum was consistent with the assigned structure, having a carbonyl stretch at 1700 cm$^{-1}$, as was the mass spectrum, having a parent peak at 144 (M+).

EXAMPLE 9

Preparation of 5-Formamido-3-chlorosulfonyl-1,2,4-triazole [Formula VII: Y=-NHC(O)H A 500 mL, 4-necked flask equipped with a mechanical stirrer, a sparge tube to introduce chlorine, a low temperature thermometer and a nitrogen outlet was charged with 7 g (48.6 mmol) of 5-formylamino-3-mercapto-1,2,4-triazole and 150 mL of 0.5M aqueous hydrochloric acid. The mixture was cooled to 0° C. with stirring and chlorine gas (160 mmol) was bubbled through while maintaining the temperature below 5° C. The mixture was diluted with water (20 mL), filtered, and the solids obtained dried to obtain 8.8 g (86 percent of theory) of the title compound as a white solid, m.p. 194°–196° C. The infrared spectrum was consistent with the assigned structure, having chlorosulfonyl associated absorptions at 1400 and 1175 cm$^{-1}$, as was the mass spectrum, having a parent peak at 212 (M+).

EXAMPLE 10

Preparation of N-(3-(((4-bromo-3-methylphenyl)amino)sulfonyl)-1H-1,2,4-triazol-5-yl)formamide [Formula VIII: R=CH$_3$; Y=-NHC(O)H]

A mixture of 4-bromo-3-methylaniline (3.72 g, 20 mmol) and 5-formamido-1,2,4-triazole-3-sulfonyl chloride (2.10 g, 10 mmol) in 50 mL of acetonitrile was refluxed under nitrogen until all of the sulfonyl chloride has been consumed (approximately 1 hr). The mixture was cooled and filtered. The precipitate was dispersed in 200 mL of 1% aqueous HCl solution and filtered again to yield the title compound as a white solid, 3.0 g (84%) m.p. 282°–284° C., M+-Br at 280.

EXAMPLE 11

Preparation of N-(3-(((4-bromo-2,6-dichloro-3-methylphenyl)amino)-sulfonyl)-1H-1,2,4-triazol-5-yl)formamide [Formula IX: X=Cl; R=CH$_3$; Y=-NHC(O)H]

A 3-necked flask equipped with a spinbar, thermometer, sparge tube to introduce chlorine and an outlet to an alkali scrubber was charged with the product of Example 10 (2 g, 5.5 mmol), 60 mL of acetonitrile and 40 mL of water. The solution was stirred rapidly and cooled in an ice water bath to 15° C. Chlorine gas (2.2 g) was bubbled through the mixture which was then allowed to stir at RT for 2 hr. The mixture was filtered and the precipitate was dried to yield the desired product as a white solid, 1.95 g (81%) m.p. >290° C., M+ at 430.

EXAMPLE 12

Preparation N-(3-(((2,6-dichloro-3-methylphenyl)amino)sulfonyl)-1H-1,2,4-triazol-5-yl)amine [Formula V: X=Cl: R=CH3]

A 3-necked flask equipped with a thermometer, reflux condenser with a nitrogen outlet, a sparge tube to introduce hydrogen and a spinbar was charged with the product of Example 11 (2 g, 4.66 mmol) and 100 mL of 95% ethanol. The mixture was stirred rapidly and purged with nitrogen and 150 mg of 10% Pd/C was added. Hydrogen gas was bubbled through the mixture while heating to reflux. After three hr of reflux the reaction was essentially complete. The mixture was purged with nitrogen and filtered. The filtrate was concentrated to yield the title compound as an off white solid, 1.5 g (98%) m.p. 198°-200° C.

What is claimed is:

1. A process for the preparation of a N-(3-(((2,6-dihalophenyl)amino)sulfonyl)-1H-1,2,4-triazol-5-yl)amine of the Formula V

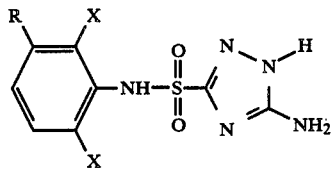

wherein
R represents H, C1-C4 alkyl or C1-C4 alkoxy; and
X independently represents Cl or Br which comprises
(a) coupling a 4-bromoaniline of the Formula (VI)

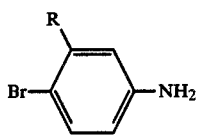

wherein
R represents H, C1-C4 alkyl or C1-C4 alkoxy with a protected 5-amino-1,2,4-triazole-3-sulfonyl chloride of the Formula (VII)

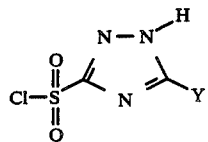

wherein
Y represents $-NH_3^{\oplus}X^{\ominus}$ or

and
R1 represents H, C1-C4 alkyl or phenyl to produce a protected N-(3-(((4-bromophenyl)amino)sulfonyl)-1H-1,2,4-triazol-5-yl)amine of the Formula (VIII)

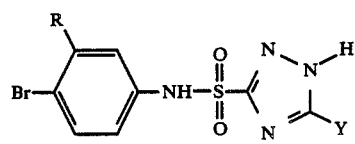

wherein
Y, R and R1 are as previously defined:
(b) halogenating the protected N-(3-(((4-bromophenyl)amino sulfonyl)-1H-1,2,4-triazol-5-yl)amine (VIII) with chlorine or bromine to produce a protected N-(3-(((4-bromo-2,6-dihalophenyl)amino)sulfonyl)-1H-1,2,4-triazol-5-yl)amine of the Formula (IX)

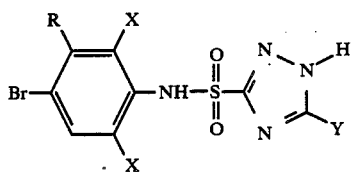

wherein
Y, R and R1 are as previously defined, and
X independently represents Cl or Br; and
(c) reducing the protected N-(3-(((4-bromo-2,6-dihalophenyl)amino)sulfonyl)-1H-1,2,4-triazol-5-yl)amine (IX) to produce the N-(3-(((2,6-dihalophenyl)amino)sulfonyl)-1H-1,2,4-triazol-5-yl)amine.

2. The process of claim 1 in which R is —CH3, —CH2CH3, —OCH3 and —OCH2CH3.
3. The process of claim 2 in which R is —CH3.
4. The process of claim 1 in which X is Cl.
5. The process of claim 1 in which Y is —NHC(O)R1.
6. The process of claim 5 in which R1 is H, —CH3 or phenyl.
7. The process of claim 1 in which R is —CH3, X is Cl, Y is —NHC(O)R1 and R1 is H, —CH3 or phenyl.

* * * * *